United States Patent
McNeirney

(10) Patent No.: US 6,200,274 B1
(45) Date of Patent: Mar. 13, 2001

(54) REMOVABLE NEEDLE RULE

(75) Inventor: John C. McNeirney, Fairburn, GA (US)

(73) Assignee: Minrad Inc., Buffalo, NY (US)

(*) Notice: Subject to any disclaimer, the term of this patent is extended or adjusted under 35 U.S.C. 154(b) by 0 days.

(21) Appl. No.: 09/111,420

(22) Filed: Jul. 7, 1998

Related U.S. Application Data

(60) Provisional application No. 60/052,821, filed on Jul. 17, 1997.

(51) Int. Cl.[7] ............................................. A61B 10/00
(52) U.S. Cl. ..................... 600/562; 600/573; 606/167; 606/172; 128/897; 604/117
(58) Field of Search .................................. 600/562, 573, 600/486; 606/167, 172, 181, 185, 485; 33/511, 512; 604/117, 164, 264, 272; 128/897, 898; 433/224, 72

(56) References Cited

U.S. PATENT DOCUMENTS

| | | |
|---|---|---|
| 3,478,435 * | 11/1969 | Cook ............................ 33/511 |
| 3,905,375 * | 9/1975 | Toyama ......................... 606/189 |
| 3,993,079 * | 11/1976 | Henriques De Gatztanondo ...... 604/164.01 |
| 4,022,191 | 5/1977 | Jamshidi ......................... 128/753 |
| 4,710,171 * | 12/1987 | Rosenberg ....................... 604/117 |
| 4,760,847 * | 8/1988 | Vaillancourt ..................... 606/185 |
| 5,040,542 | 8/1991 | Gray ............................. 128/754 |
| 5,217,438 | 6/1993 | Davis et al. .................... 604/198 |
| 5,312,374 * | 5/1994 | Gurmarnik ....................... 604/264 |
| 5,320,608 * | 6/1994 | Gerrone ......................... 604/117 |
| 5,336,206 * | 8/1994 | Shichman ........................ 604/534 |
| 5,383,859 * | 1/1995 | Sewell, Jr. ..................... 604/164 |
| 5,454,374 * | 10/1995 | Omachi .......................... 600/486 |

* cited by examiner

*Primary Examiner*—Cary O'Connor
*Assistant Examiner*—Charles Marmor, II
(74) *Attorney, Agent, or Firm*—Hodgson, Russ, Andrews, Woods & Goodyear LLP

(57) ABSTRACT

A measuring and gauging device for ruling the depth of penetration of the needle of an invasive instrument into a patient's body is also used to fit over the needle and the needle tip to protect against needle damage, accidental sticking of the user's fingers and puncture of the package within which the invasive instrument is stored and shipped.

10 Claims, 4 Drawing Sheets

REMOVABLE NEEDLE RULE

CROSS-REFERENCE TO A RELATED APPLICATION

Applicant hereby claim priority on earlier filed provisional patent application Ser. No. 60/052,821, filed Jul. 17, 1997, which is incorporated herein by reference.

BACKGROUND OF THE INVENTION

1. Field of the Invention

The present invention relates generally to a device for ruling off the length of a needle or cannula, and more specifically to devices for ruling that portion of a needle or cannula which is to be inserted into a patient such that the portion to be inserted into the patient can be gauged and marked with a needle stop prior to insertion.

2. Description of the Related Art

Needles are commonly employed to obtain biopsy specimens for laboratory evaluation. This entails a surgical procedure which requires that the surgeon know precisely the depth to which the needle is inserted in the patient's tissue to be sure that a proper specimen is obtained. Typically, spaced markings are provided along the surface of the needle to indicate the depth of penetration of its tip. A depth stop may be employed to limit penetration of the needle to the desired depth.

The practice of providing spaced markings along the surface of the needle is attended by significant disadvantages. A primary disadvantage is the difficulty of reading such markings. The limited surface area of a typical needle necessarily imposes constraints on the size of the markings which may be etched thereupon. Small markings are difficult for a surgeon to read with the naked eye. The low contrast between the needle surface and the marking exaggerates this problem. The problem is made worse if lighting conditions are poor, or if the needle is held in a position which causes light to be reflected from it.

Another common practice involving such needles is that of providing a protective covering, or shield, over the needle and needle tip to protect against needle damage, accidental sticking of the user's fingers, and puncture of the package within which the needle is shipped. A shield is placed over each individual needle for shipping, handling, and storage purposes, and is removed and discarded prior to use of the needle.

Some protective coverings were designed to perform a dual function: to seal the needle portion of an instrument and gauge the depth of penetration of the needle. For example, U.S. Pat. No. 4,022,191 to Jamshidi discloses a sleeve guard made of a frangible material. The outer circumference of the shank of the sleeve guard has a plurality of spaced apart circumferential grooves disposed at spaced intervals along the length of the sleeve guard. The grooves are formed in such a way that the depth of the grooves is sufficient to permit the shank to break upon flexure. The breakage forms an open ended sleeve which exposes a predetermined length of the needle and serves as a stop for the needle when it enters the body of a patient.

Some of the clear disadvantages of that sleeve guard are the need to complicate the manufacturing process by having to cut the grooves, the necessity to break the shank to expose a part of the needle for insertion, the limited number of the available needle lengths which can be exposed depending on the number and a spacing of the grooves.

Another solution, disclosed in U.S. Pat. No. 5,217,438 to Davis et al., provides a stop for a biopsy needle or the like, comprising a continuous wire spring formed in a series of adjacent coils. The internal diameter of each of the coils in the unstressed condition is selected to be less than the outer diameter of the shaft on the needle. The spring has two end portions that can move toward each other and expand the coils radially. The spring with expanded coils may be moved along the shaft of the needle to a particular location. Releasing the two end portions causes the spring to grip the surface of the needle shaft, therefore, providing a depth gauge for the portion of the needle which will be inserted into a patient.

The disadvantage of the spring device of the Davis et al. is the necessity to have a separate rule to measure the insertion depth of the needle. Additionally, the stress exerted on the tubular shaft of the needle by the spring can damage or break the needle.

Therefore, a need remains for a simple, easy to use, and clearly visible means by which a surgeon, or operator may rule the desired penetration depth of a needle prior to insertion of the needle in a patient's body. Coincidentally, an opportunity exists for further advantageous use of the protective shield within which needles and needle tips are enclosed for shipping and storing.

SUMMARY OF THE INVENTION

The present invention provides a device for ruling a portion of a needle to be inserted into a patient's body, the device comprising a ruler portion and a needle guide portion. The ruler portion includes a scale portion marked along the longitudinal axis of the ruler portion to indicate increments of measure. The needle guide portion permits an operator to align the tip of a needle with the scale portion at the increment which represents the desired insertion depth of the needle.

The present invention also provides a shield or covering a needle and needle tip during shipping which serves both a protective function for the needle itself, and at the same time, provides a means for ruling the length of the needle to obtain the desired insertion depth.

DETAILED DESCRIPTION OF THE INVENTION

Figure 1:
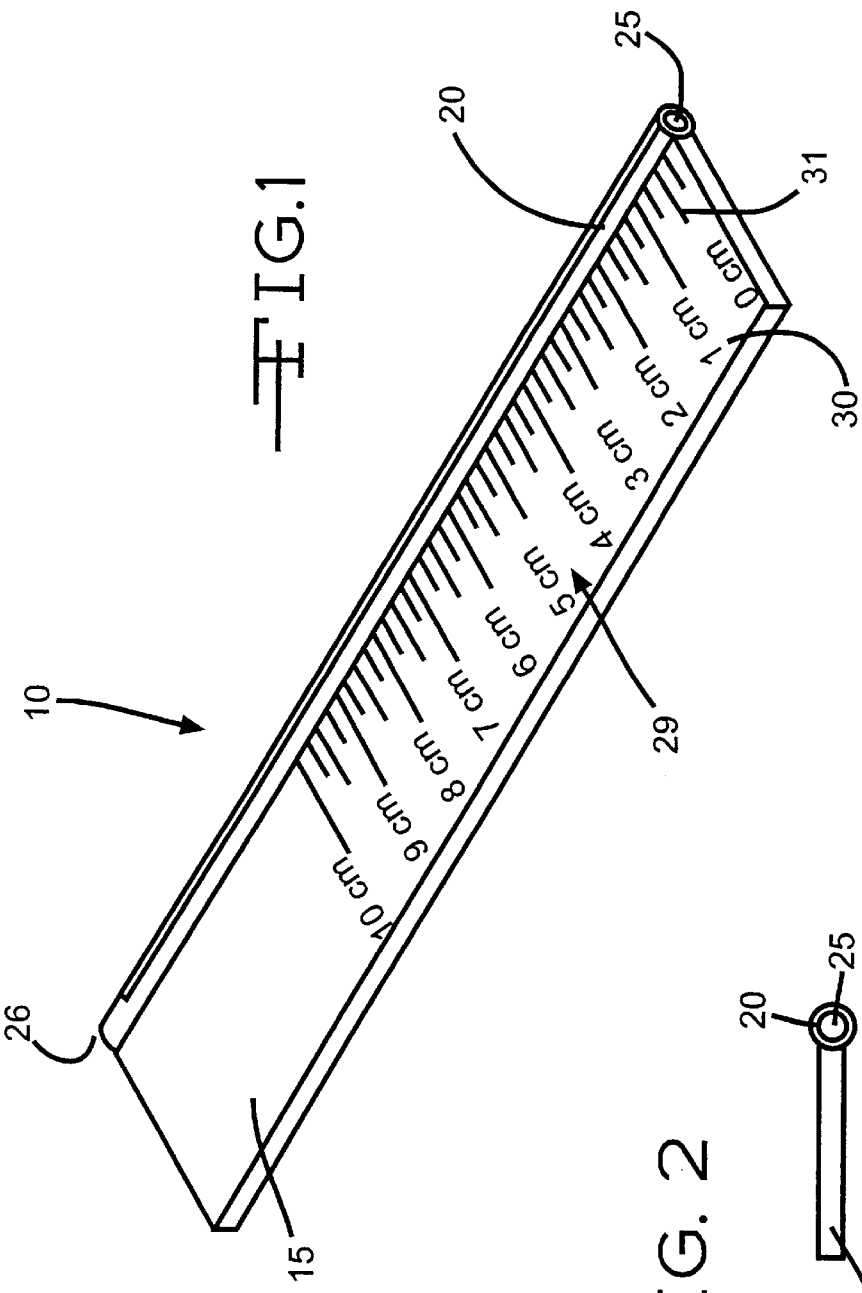
FIG. 1 is a perspective view of the removable needle rule of the present invention.

FIG. 1 shows a removable needle rule 10 according to the principles of the present invention. Rule 10 comprises a ruler portion 15 and a needle guide portion 20. Ruler portion 15 includes a scale component 29 drawn along the longitudinal axis of ruler portion 15 and marked in the increments desired. Rule 10 of FIG. 1 is marked in increments (as shown at 31) of 25 mm, with whole centimeters being indicated numerically (as shown at 30). Other standards of measurements, such as the English system could be used in the present invention. Markings could be applied in smaller or larger increments.

Ruler portion 15 may be constructed from any suitable material such as plastic, wood or composite materials, but is preferably constructed from a lightweight plastic material. Numerical indications 30 and increments or graduations 31 are preferably large enough and bold enough to be clearly seen and quickly discernable in a medical office or operating room setting.

Affixed to ruler portion 15 is needle guide portion 20 constructed in a way that allows a user to see a needle inside guide portion 20. Preferably, needle guide portion 20 is constructed from a transparent material, such as transparent plastic, so that the entire length of a needle inserted therein may be readily visible to the naked eye. Needle guide portion 20 may be affixed to ruler portion 15 by conventional means such as adhesives, or other means well known in the art. Needle guide portion 20 is preferably affixed along one side of ruler portion 15, adjacent to graduations 31, and extending longitudinally along the length of ruler portion 15. Alternatively needle guide portion 20 and ruler portion 15 can be manufactured as one piece, eliminating the need to use adhesive to assemble the rule. Furthermore, needle guide portion 20 may be positioned longitudinally along any axis of ruler portion 15 such that an operator may visually align the tip 56 of needle member 55 with graduations 31, as shown in FIG. 3.

Figure 2:
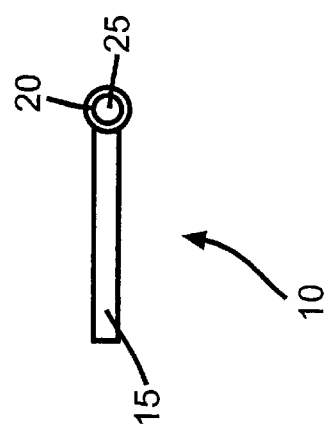
FIG. 2 is an end elevation view of the removable needle rule of the present invention.

Needle guide portion 20 is preferably cylindrical in shape and has a hollow interior portion extending therethrough, such that an operator may removably insert the tip of a needle at the proximal end of needle guide portion 20 through opening 25 (best illustrated in FIG. 2). The operator may then move the tip of the needle toward the distal end of needle guide portion 20 such that the tip may, but preferably does not, extend beyond distal opening 26. Needle guide portion 20 may be adapted to fit and cover a needle and needle tip so as to protect the needle during shipping, storage and handling. In that case it may not be desirable to include distal opening 26, but to have a closed distal end instead.

A surgical instrument such as a biopsy needle may be provided with needle rule 10 at the time it is packaged and shipped to its destination. When shipped in this manner needle rule 10 may serve as both a rule and a shield, or protective covering for a needle 55, as illustrated in FIG. 3.

Figure 3:
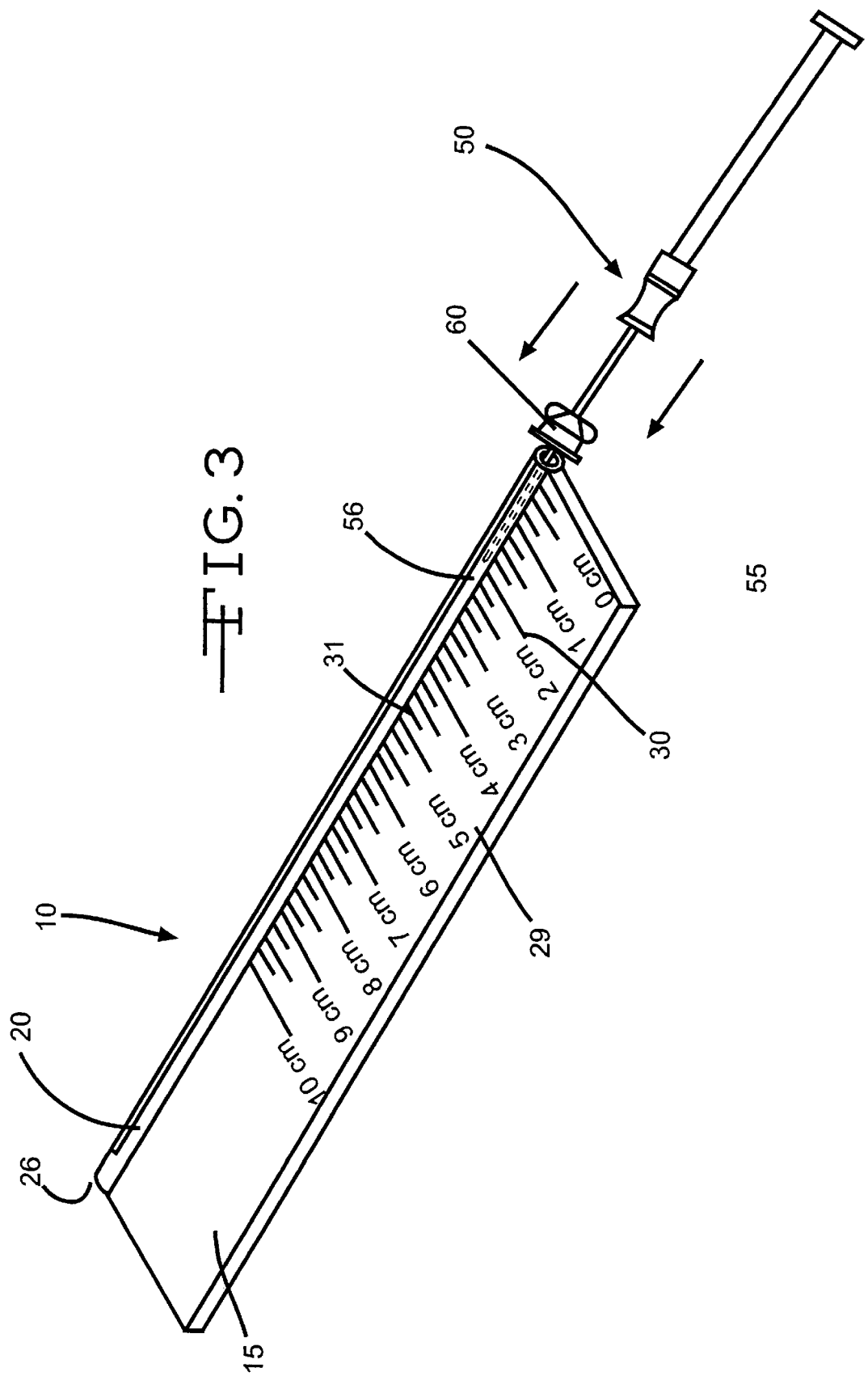
FIG. 3 is a perspective view of the removable needle rule as it appears in use with a needle.

FIG. 3 shows removable needle rule 10 as used in conjunction with a surgical instrument 50, such as a biopsy needle. In use, an operator or surgeon first determines the desired depth of penetration (shown in FIGS. 3 and 4 as d) of needle 55 into a patient. Such determination is generally made using video imaging, or other techniques known in the surgical arts. Once the desired penetration depth d is determined, needle rule 10 may be used to gauge the needle, that is, to rule off that portion of the needle which will be allowed to percutaneously enter that patient's body, and to mechanically limit penetration of the remaining length of the needle.

For example, if the desired penetration depth of a needle into a patient's body is determined to be 2 cm, i.e. d=2 cm, an operator would insert needle 55 of surgical instrument 50 through opening 25 into the hollow interior of needle guide portion 20 of needle rule 10. The operator would then advance needle 55 through needle guide portion 20 until tip 56 of needle 55 is aligned with the graduation 31 which indicates 2 cm, the desired penetration depth of needle 55 into the patient's body. During this procedure the operator visually monitors the advancement of needle 55 and tip 56. When the operator sees tip 56 reach the graduation 31 which indicates the desired insertion depth d, the operator stops advancing the needle.

While holding tip 56 of needle 55 steadily in alignment with the desired graduation 31, the operator then adjusts a needle stop 60 so that it rests contiguously with needle guide portion 20 at opening 25. Needle stop 60 may be any of a variety of needle stops commonly used in the surgical arts.

After needle stop 60 is secured in contiguous relation to needle guide portion 20, removable needle rule 10 is separated from surgical instrument 50 by simply sliding needle member 55 out of needle guide portion 20, or vice versa. In that manner, the desired insertion depth d is gauged and marked off (by setting needle stop 60) so that insertion of needle member 55 into a patient's body to a depth further than the desired 2 cm will be effectively prevented.

Figure 4:
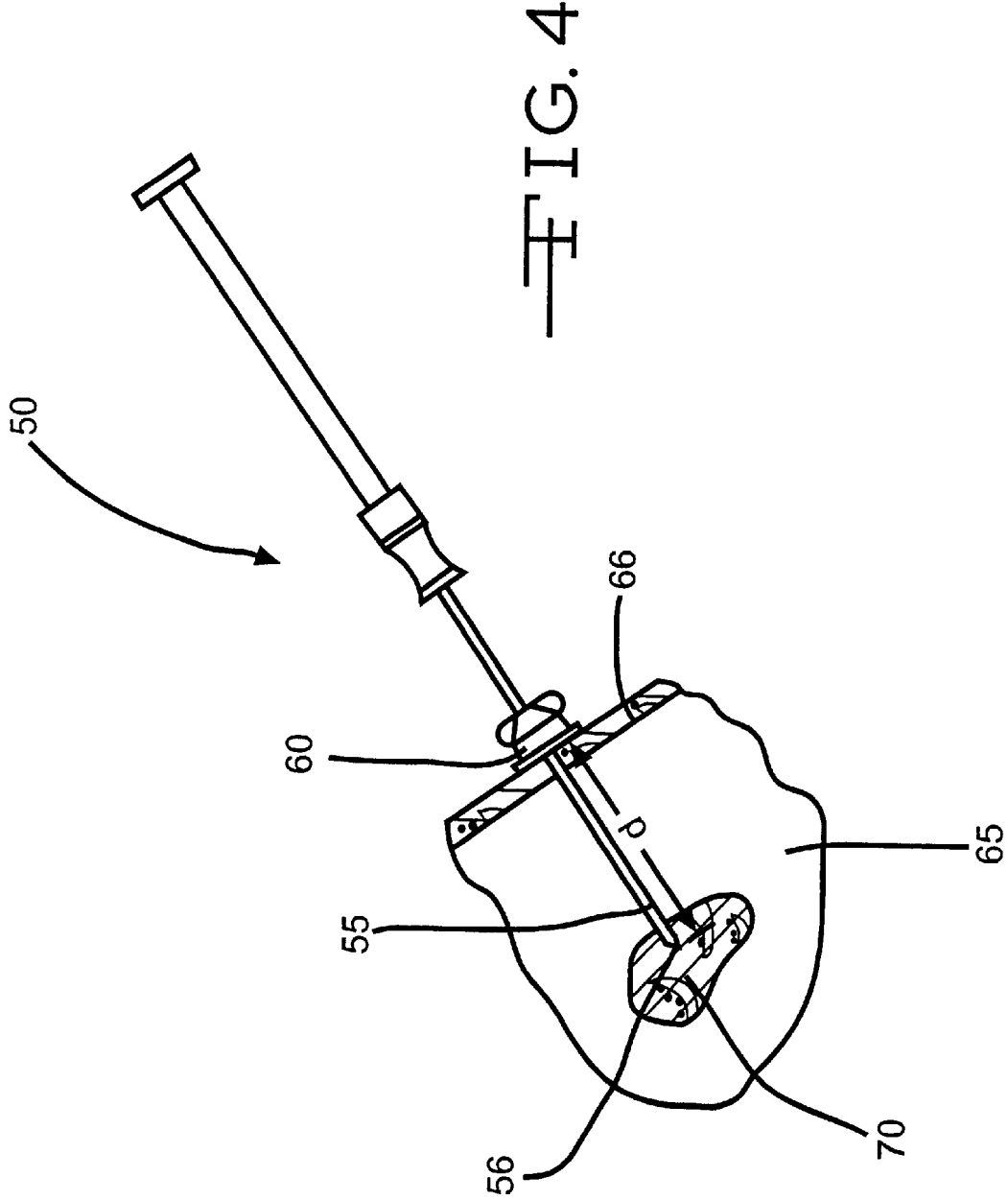
FIG. 4 is a perspective view of a needle inserted into the body of a patient to the desired depth.

As best illustrated in FIG. 4, the operator may then insert needle member 55 into a patient's body 65 through the patient's skin 66. FIG. 4 shows surgical instrument 50 as it appears after percutaneous insertion into the patient's body 65 to a desired depth d, extending toward a target 70, and after having been gauged and set by means of removable needle rule 10.

Figure 5:
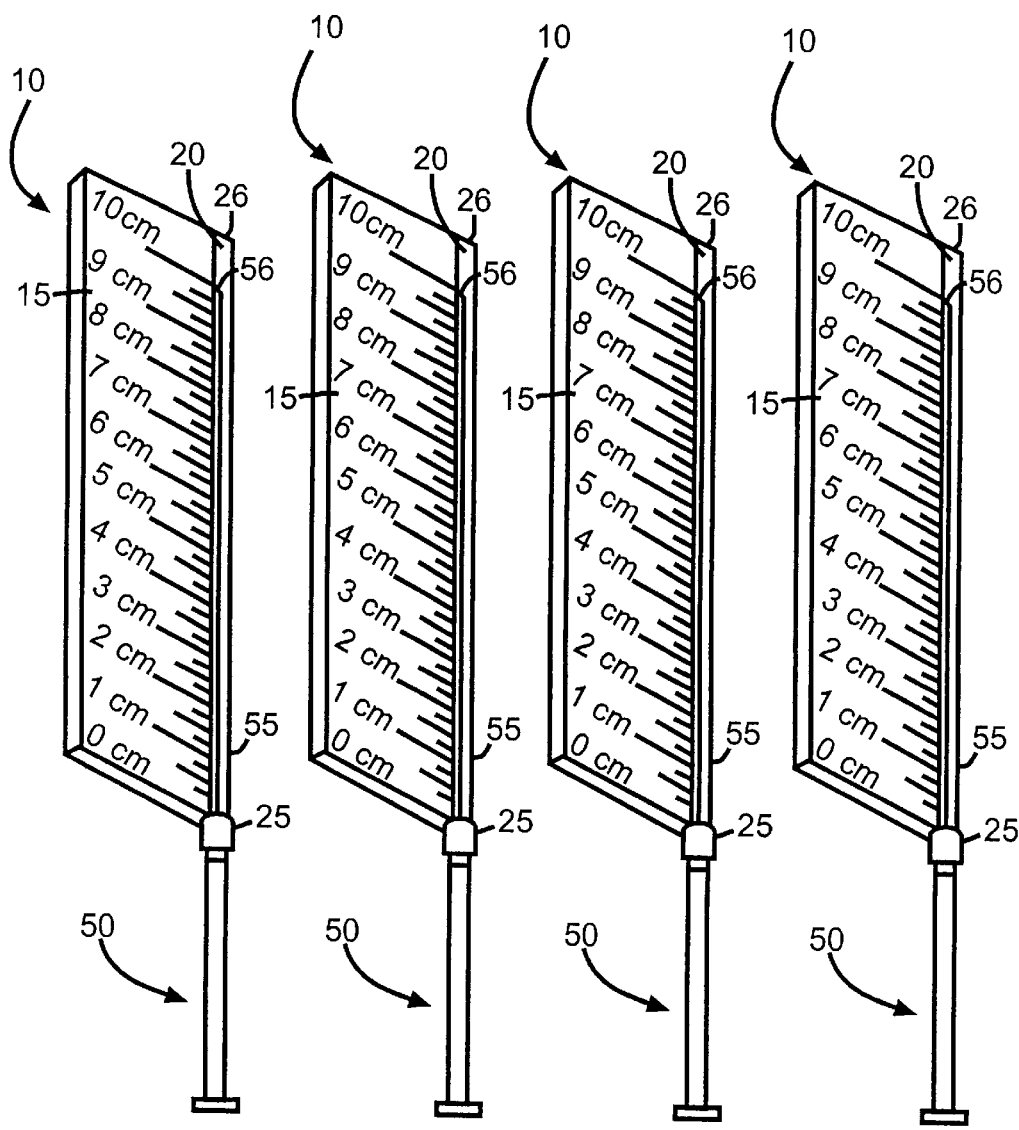
FIG. 5 is a perspective view of a plurality of the devices of the present invention in use as a needle rule and a shield.

FIG. 5 shows a plurality of removable needle rules 10 embodied as shields, i.e. protective covers for needles 55 as they might appear ready for shipment. Each needle 55 of each surgical instrument 50 is covered by needle guide portion 20 of removable needle rule 10. In this case, opening 26 of guide portion 20 may be closed to prevent dust or other debris from entering needle guide portion 20 and contaminating needle 55. Surgical instruments 50 may then be shipped and stored while thus protected. When it is desired to use one of the surgical instruments 50, the operator selects one surgical instrument 50 for use and utilizes ruler portion 15 to measure and gauge the desired penetration depth of needle 55.

Accordingly, needle rule 10 serves a dual purpose. First, it fits over needle 55 and needle tip 56 to protect against needle damage, accidental sticking of the user's fingers, and puncture of the package within which the needle is shipped. In addition, removable needle rule 10 provides a convenient and easy-to-use measuring and gauging device for ruling the depth of needle penetration into a patient's body.

While the invention has been described in connection with specific embodiments thereof, it will be understood that this is by way of illustration and not limitation and that the scope of the invention should be construed as broadly as the prior art will permit.

What is claimed is:

1. A kit comprising an invasive instrument and a measuring device, the invasive instrument having a penetrating element and a stopping element movable along the penetrating element, the measuring device comprising a ruler portion having a scale component including a marking disposed along an axis of the ruler portion, and a separate hollow guide portion being contiguous with and offset from the ruler portion and disposed along the said axis, the hollow guide portion having a first opening at a first end of the guide portion through which the penetrating element of the invasive instrument can be inserted into the guide portion, the hollow guide portion being of a material allowing visual inspection of the extent to which the penetrating element is inserted therein, so that the stopping element can be adjusted to rest contiguously with the opening of the guide portion whereby the position of the stopping element is indicative of a predetermined length of the penetrating element.

2. The kit of claim 1, wherein the hollow guide portion and the ruler portion are integrally constructed.

3. The kit of claim 1, wherein the marking comprises graduations of equal increments indicating increasing magnitude.

4. The kit of claim 1 further comprising the hollow guide portion having a second opening disposed at the second end of the guide portion.

5. The kit of claim 1, wherein the second end of the hollow guide portion is sealed.

6. The kit of claim 1, wherein the hollow guide portion is of substantially transparent material.

7. The kit of claim 1, wherein the axis of the ruler portion is a longitudinal axis.

8. A method of ruling a predetermined length of a penetrating element of an invasive instrument by a measuring device, the invasive instrument having a stopping element, the measuring device comprising a ruler portion having a scale component and a separate hollow guide portion contiguous with and offset from the ruler portion, the method comprising:

removably inserting the penetrating member into the guide portion through an opening at one end of the guide portion;

aligning the tip of the penetrating member with a predetermined location on the scale component of the ruler portion by visually monitoring the movement of the tip along within the separate and offset guide portion in relation to the scale component of the ruler portion; and adjusting the stopping element to rest contiguously with the opening of the guide portion so that the position of the stopping element is indicative of the predetermined length of the penetrating element.

9. The method of claim 8 further comprising a step of removing the penetrating member from the guide portion.

10. The method of claim 8, wherein the hollow guide portion is of substantially transparent material.

* * * * *